United States Patent [19]

Coufal et al.

[11] Patent Number: 5,603,316
[45] Date of Patent: Feb. 18, 1997

[54] DISABLING APNEA VOLUME SOFTWARE

[75] Inventors: Delwin T. Coufal; Karl N. Knauf, both of Madison, Wis.

[73] Assignee: Ohmeda Inc., Liberty Corner, N.J.

[21] Appl. No.: 408,450

[22] Filed: Mar. 22, 1995

Related U.S. Application Data

[63] Continuation of Ser. No. 126,953, Sep. 27, 1993, abandoned.
[51] Int. Cl.$^6$ .......................... A61M 16/00; A62B 9/00; A62B 27/00; G08B 3/00
[52] U.S. Cl. ................ 128/204.23; 128/202.22; 128/205.23; 128/716; 364/413.02
[58] Field of Search ...................... 128/716, 719, 128/720, 200.24, 202.22, 203.14, 203.28, 204.18, 204.21, 204.22, 204.23, 205.13, 205.17, 204.26, 205.23; 364/413.02, 413.03

[56] References Cited

U.S. PATENT DOCUMENTS

| | | | |
|---|---|---|---|
| 3,985,131 | 10/1976 | Buck et al. | 128/204.23 |
| 4,256,100 | 3/1981 | Levy et al. | 128/204.21 |
| 4,323,064 | 4/1982 | Hoenig et al. | 128/204.21 |
| 4,537,190 | 8/1985 | Caillot et al. | 128/204.22 |
| 4,883,051 | 11/1989 | Westenskow et al. | 128/204.21 |
| 4,986,268 | 1/1991 | Tehrani | 128/204.22 |
| 5,129,390 | 7/1992 | Chopin et al. | 128/204.21 |
| 5,355,893 | 10/1994 | Mick et al. | 128/719 |
| 5,394,881 | 3/1995 | Block, Jr. | 128/716 |
| 5,505,199 | 4/1996 | Kim | 128/716 |
| 5,534,851 | 7/1996 | Russek | 128/202.22 |

FOREIGN PATENT DOCUMENTS

| | | | |
|---|---|---|---|
| 228447 | 10/1985 | Germany | 128/204.22 |
| 8606638 | 11/1986 | WIPO | 128/204.22 |

*Primary Examiner*—Kimberly L. Asher
*Attorney, Agent, or Firm*—Roger M. Rathbun; R. Hain Swope

[57] ABSTRACT

A system for allowing a user to disable an apnea alarm in an anesthesia system when the anesthesia ventilator is in the mechanical ventilation mode. The system takes advantage of the redundancy of both a CO2 monitor and a volume monitor triggering the apnea alarm based upon a predetermined fault condition. The inventive system allows the user to disable the apnea alarm based upon a signal from the volume monitor to alleviate the problem of spurious alarm signals from the volume monitor. The attempt to disable the volume monitor fault signal to the apnea alarm is prevented, however, without a system check by a CPU to insure that the CO2 monitor is, in fact, fully operational and capable of sending its fault signal to the apnea alarm to trigger that alarm. The system continuously checks the CO2 monitor and immediately restores the viability of the volume monitor as a trigger for the apnea alarm at any time the CO2 monitor becomes disabled and is unable to trigger the apnea alarm itself. Thus the volume monitor based apnea alarm may be disabled by the user without compromising the alarm function of the overall anesthesia system.

7 Claims, 2 Drawing Sheets

DISABLING APNEA VOLUME SOFTWARE

This is a continuation of application Ser. No. 08/126,953 filed Sep. 27, 1993, now abandoned.

BACKGROUND OF THE INVENTION

This invention relates to medical equipment and, more particularly, to integrated anesthesia machines where a patient is induced and retained under anesthesia and where various parameters of the patient and the anesthesia machine are continuously monitored.

Anesthesia machines and/or systems are regularly used to maintain a patient undergoing surgery in a state of anesthesia and include various components, including vaporizers, to produce an anesthetic vapor from a liquid anesthetic, flowmeters and control valves for introduction of a carrier gas to carry the anesthetic to the patient and a series of monitors that carefully monitor various conditions of the patient and the status and operating condition of the anesthesia system itself.

Current anesthesia machines carry a variety of such monitors, including $CO_2$ monitors, volume monitors, oximeters, blood pressure monitors, airway pressure monitors and the like. Many of the monitors are integrated into the anesthesia machine in order to localize all such monitors into a convenient location and to make use of the function of each of the monitors. In addition, such machines also provide a variety of alarms that are activated to alert the user as to a condition that should be investigated so as to protect the patient who, for obvious reasons, is unable to alert the attending personnel as to any such problems.

The present invention relates specifically to the alarm known as an apnea alarm and which signals an alarm condition when there is an indication that breathing has ceased or has been reduced to an unacceptable level. At present, the apnea alarm is commonly triggered based upon signals from two monitors, the $CO_2$ monitor and the volume monitor. The $CO_2$ monitor analyzes the level of $CO_2$ in the patient's breathing circuit for both inspired and expired gasses and that $CO_2$ level produces a well known wave shape during normal ventilation. The volume monitor continuously monitors the volume of gas expired by the patient and its transducer or sensor is also located in the patient breathing circuit near the patient.

As indicated, both the $CO_2$ monitor and the volume monitor can trigger an alarm to indicate an apnea condition. Typically, the apnea alarm is triggered if the volume monitor does not indicate an increase in exhaled volume from the patient within a specific period of time, for example 30 seconds. Similarly, the $CO_2$ monitor must receive and monitor the representative waveform within, for example, the same period of time 30 seconds. If the well known, representative waveform is not present during that period, the apnea alarm is triggered by the $CO_2$ monitor.

As seen, therefore, the apnea alarm can be triggered by the recognition of fault conditions by either or both of the volume alarm and the $CO_2$ alarm thereby establishing somewhat redundant systems triggering that alarm.

There is, in such anesthesia systems, a problem with spurious alarms, that is alarms that are triggered and which alert the personnel to a apnea condition wherein fact the problem is not an apnea condition and the patient is not experiencing an apnea condition. Such spurious alarms are annoying to the attending personnel since their attention is diverted to investigating the alarm condition only to find out that no alarm condition actually existed. Eventually personnel could ignore such alarms or give such alarm less than full attention on the belief that a spurious alarm was being repeated. Obviously, such a situation is not desirable.

One typical spurious alarm occurs with the apnea alarm based upon the volume monitor. A reason for the spurious apnea alarms based upon the volume monitor is that its sensor is positioned in the exhalation line of the patient circuit where the exhalation is returning from the patient to the bellows of the anesthesia machine. Often leaks occur in the exhalation flow stream and, typically, uncuffed tracheal tubes leak around the outside of such tubes such that all of the exhalation does not pass through the volume monitor sensor. The volume alarm thus interprets the lack of a predetermined volume of exhalation as a fault condition and triggers the apnea alarm even though the patent is being breathed normally.

Accordingly, it would be advantageous to be able to selectively, at the users choice, disable the apnea alarm based upon the volume monitor to prevent such spurious alarms, however, obviously, one cannot do so where the overall alarm functions of the anesthesia system would be compromised.

In present anesthesia machines, it is not therefore possible to disable or turn off the apnea alarm based upon the volume monitor when the anesthesia system is utilizing mechanical ventilation, that is where the anesthesia ventilator is breathing for the patient. If, on the other hand, the anesthesia system is in the bagging mode, that is the mechanical ventilator is not being used but instead the doctor is manually bagging the patient, it is possible to disable the apnea alarm based upon the volume monitor since in the bagging mode, it is assumed that the physician is present at the side of the patient and is visually monitoring the patients condition. As such, the alarms are not as necessary as the physician will immediately detect the apnea condition in the patient and be able to take any corrective action needed.

Accordingly, therefore, the problem of spurious apnea alarms is limited to the time in which the anesthesia ventilator is in the mechanical ventilation mode and at that time, spurious alarms are possible based upon the volume monitor.

SUMMARY OF THE INVENTION

In accordance with the present invention, the aforementioned difficulties relating to spurious apnea alarm conditions based upon the volume monitor have been alleviated by recognizing and taking advantage of the redundancy between the triggering of the apnea alarm based upon fault conditions sensed by the volume monitor and the $CO_2$ monitor.

Accordingly, the present system allows the user to, in fact, disable or turn off the apnea alarm based on the volume monitor even when the anesthesia ventilator is in the mechanical ventilation mode without compromising the overall alarm scheme of the anesthesia system. The present system, through a central processing unit (CPU) queries the $CO_2$ monitor to assure that it is in the active mode, that is not undergoing a self check or calibration cycle, or is for some other reason not functioning properly, and when that query comes back affirmative, validates the users selective disabling of the apnea alarm based upon the volume monitor. In this manner, the user is assured that apnea is still being monitored, that is, by means of the $CO_2$ monitor and that the volume monitor will thus not be causing the annoying spurious alarms.

Thus the system checks internally to determine that the $CO_2$ monitor is in operation and is capable of recognizing a predetermined fault condition and capable of triggering the apnea alarm before it will allow the user to disable the volume monitor's signal to the apnea alarm.

Therefore, the present system allows the user to shut off the volume controlled apnea alarm only under certain conditions and continues to query the $CO_2$ monitor to insure that it remains fully operational. If it is not operational at any time, or ceases to be operational, the present system will, on its own, force the volume monitor active so that it will carry out the function of triggering the apnea alarm upon detection of a fault condition.

DETAILED DESCRIPTION OF THE PREFERRED EMBODIMENT

Figure 1:
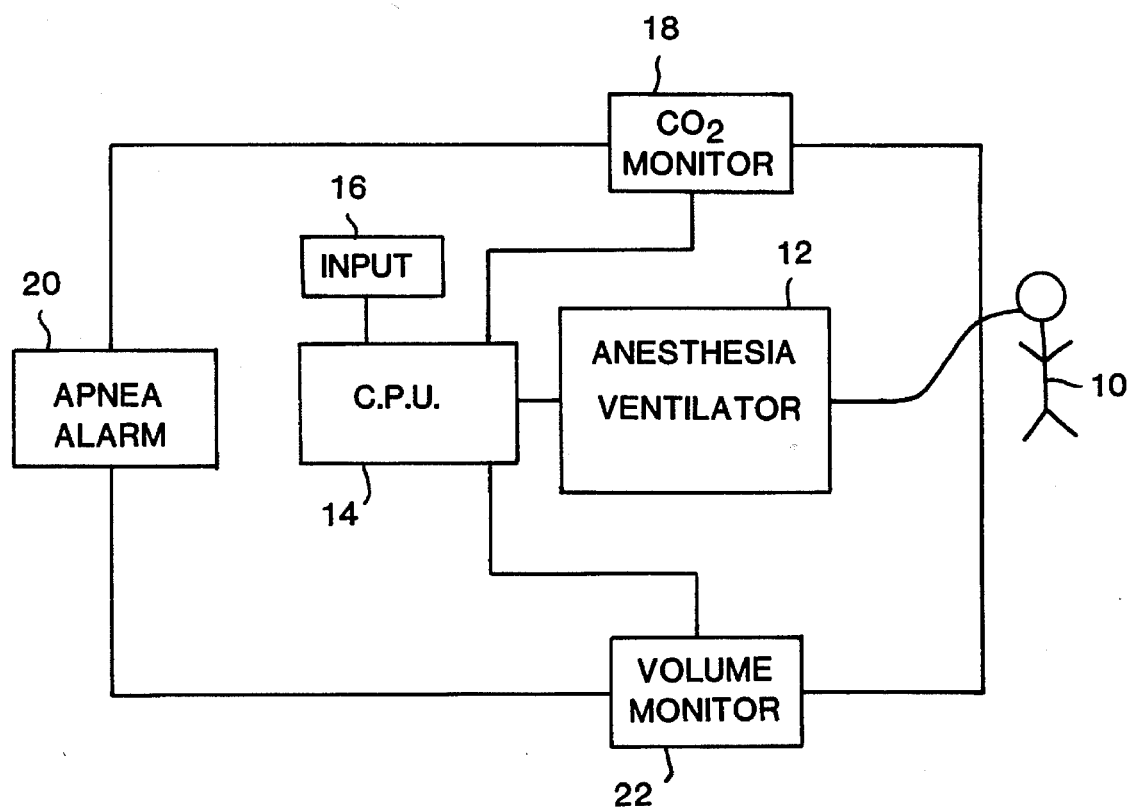
FIG. 1 is an overall block diagram of the relevant portion of an anesthesia system to which the system of the present invention pertains.

Turning first to FIG. 1, there is shown block diagram of the basic components of an anesthesia system in which the present invention is used. As shown, therefore a patient 10, who is under anesthesia, is ventilated by an anesthesia ventilator 12. During such anesthesia, the patient 10 is administered the anesthetic by means of an anesthesia machine or system that, as described, includes anesthetic vaporizers, flow meters, valves and the like used to introduce an anesthetic as a gas into an oxygen containing carrier gas. The anesthetic itself is initially in the form of a liquid and the anesthesia machine therefore also contains vaporizers to convert the liquid into a gas at the desired concentration to the patient.

Other parts of a typical anesthesia machine includes various monitors to monitor the wellbeing of the patient as well as the functioning of the anesthesia machine itself. As a part of the overall anesthesia system, the anesthesia ventilator 12 breathes for the patient, that is, the ventilator 12 provides timed breaths to carry out the normal breathing of the patient since the patient under anesthesia is unable to carry out spontaneous breathing.

Anesthesia ventilator 12 is generally controlled by a central processing unit (C.P. U.) 14 and which controls the timing of the anesthesia ventilator 12 as well as the mode thereof. As an example, the user may chose to manually breath the patient 10 by means of a bag, not shown, where the user fills the patient's lungs by squeezing a bag to force air into the patients lungs. At such time the user, normally a physician, such as an anesthesiologist, is positioned alongside the patient 10 and therefore can observe for vital signs and can personally monitor the patients wellbeing during anesthesia.

An input 16, such as a keyboard, enables the physician to control the C.P.U. and to enter data, alarm settings, ventilator modes and the like, as desired by the physician. One of the selections made by the physician is the mode of the anesthesia ventilator 12 that is, a selection may be made to use the anesthesia ventilator 12 in the mechanical ventilation mode where the anesthesia ventilator 12 breathes for the patient or the bagging mode where the anesthesia ventilator 12 basically is in a standby mode and the physician caries out the breathing of the patient through the bagging function.

As will be seen, the input 16 also has other functions in carrying out the present invention.

A $CO_2$ monitor 18 is provided in the anesthesia system to continuously monitor the level of $CO_2$ in the patients inhalation and exhalation streams and the sensor or transducer is located near the patient and within the patient circuit. The $CO_2$ level in the patient circuit is useful for a variety of purposes in monitoring a patient under anesthesia, however, for the present invention, the relevant purpose of the $CO_2$ monitor 18 is to recognize an alarm condition in the $CO_2$ level in the patient circuit and trigger an apnea alarm 20.

Basically, the apnea alarm 20 is a audible and/or visual alarm that signals the attending physician that there is some cessation of breathing of the patient and alerts the physician to take immediate action to check the patients breathing. With the $CO_2$ monitor, that apnea alarm 20 is triggered by the $CO_2$ monitor 18 recognizing that the normal representative waveform that should be present with a normal breathing patient is not present within a specified period of time. That is, the $CO_2$ monitor recognizes a typical wave form of the concentration of $CO_2$ that occurs with each normal breath of the patient. If that waveform is not present for a period of time, for example, thirty seconds, the $CO_2$ monitor recognizes that something is wrong and triggers the apnea alarm 20 to alert the attending physician.

A second trigger means for the apnea alarm 20 is by means of a volume monitor 22, again, also tied in to the patient circuit and which monitors the volume of air expired by the patient at each breath. Again, a period of time is used, and again may be thirty seconds to trigger apnea alarm 20. If, for example, the volume monitor 22 has not seen a predetermined threshold of gas volume exhaled by the patient within that period of time, it recognizes that a fault condition exists and triggers apnea alarm 20 to alert the attending physician.

Accordingly, as can be seen, the apnea alarm 20 is triggered by somewhat redundant functions, both by the $CO_2$ monitor 18 and by the volume monitor 22. As outlined, the volume monitor 22 typically gives spurious readings and it is advantageous to therefore to allow the user the option of disabling the apnea alarm 20 based on the input from the volume monitor 22. The system, however, cannot allow such action when the anesthesia ventilator is in the mechanical mode unless there is sufficient assurance that the redundancy is present, that is, that the apnea alarm will still be triggered by the $CO_2$ monitor 18.

Figure 2:
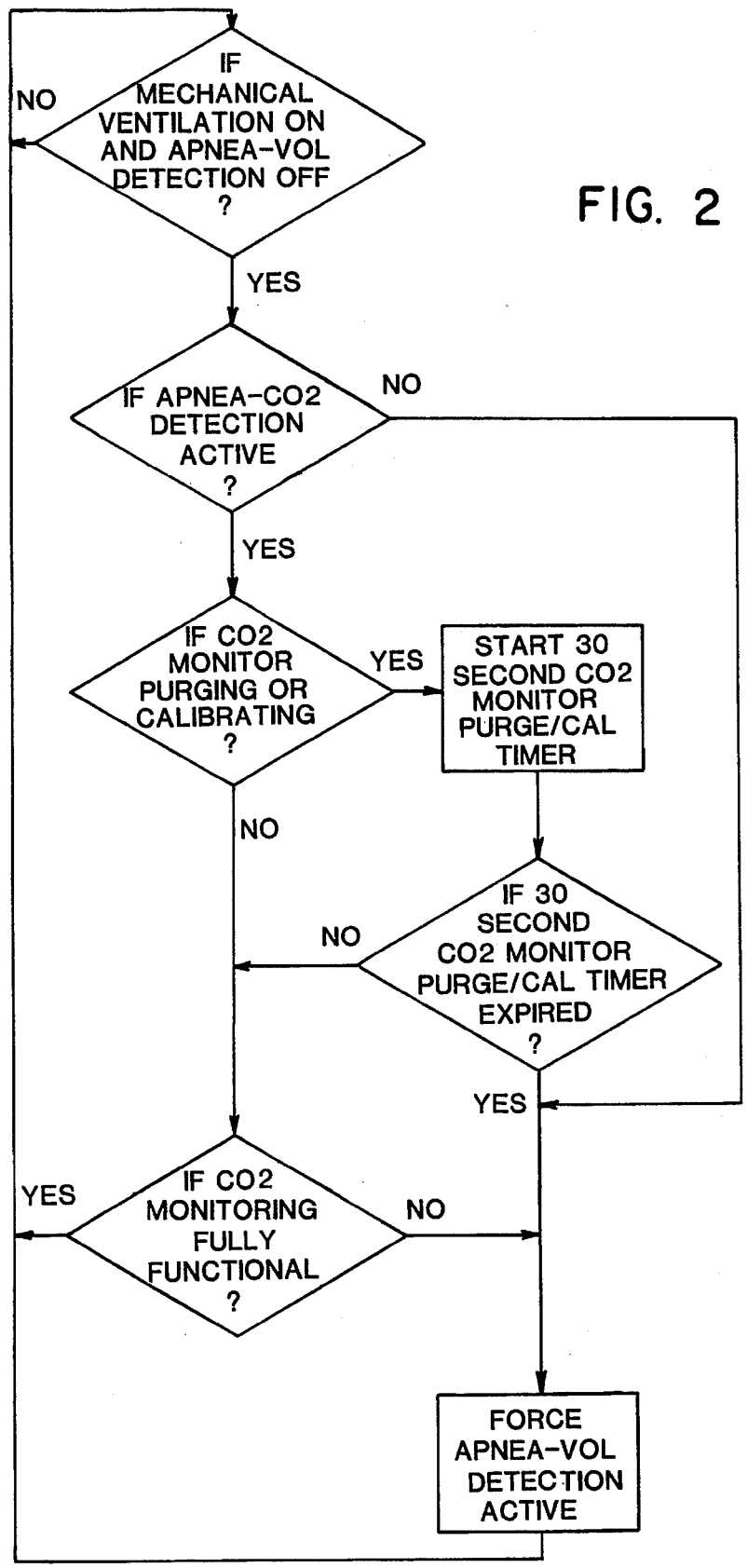
FIG. 2 is a flow chart showing the operation of the system of the subject invention.

Turning now to FIG. 2, taken in connection with FIG. 1, a flow chart is shown that describes the system of the present invention and which allows the user to disable or turn off the use of the volume monitor as a feed to trigger the apnea alarm 20 without compromising the alarm function of the anesthesia system.

The present system is operative when a user is operating the anesthesia ventilator 12 in the mechanical ventilation mode, that is, the anesthesia ventilator 12 is supplying the breaths to the patient. As previously explained, the system does not have an effect, and is not needed, when the anesthesia system is in the bagging mode and the anesthesia ventilator 12 is not being used. At such time, as in the past, the physician can freely turn off or disable the apnea monitor 20 based on input from the volume monitor 22 to thereby avoid spurious alarms.

In the present system, the physician can, by using the input 16, signal the C.P.U. to disable the volume monitor 22 from triggering the apnea alarm 20. If, of course, the CPU determines that the anesthesia ventilator 12 is not in the mechanical ventilation mode, the present system will not function since it is not needed. The trigger mechanism from the volume monitor 22 to the apnea alarm 20 will simply be disabled. If, on the other hand, the anesthesia ventilator 12 is in the mechanical mode, the CPU will query the CO2 monitor to see if it is active and therefore operational to itself trigger the apnea alarm under its criteria for a fault condition.

If the response is no, indicating that the CO2 monitor 18 is not functioning, then the CPU will immediately force the volume monitor 22 active to signal its fault condition to trigger the apnea alarm 20. Thus the operator's attempt to disable the triggering signal from the volume monitor 22 to the apnea alarm 20 is not accepted by the anesthesia system since it would, in effect, leave no monitor active to trigger the apnea alarm 20.

In the alternative, if the CPU determines that the CO2 monitor is active, it will then further inquire as to whether the CO2 monitor is in a purge cycle or a calibration cycle, both of which are self functioning systems that take a short period of time, but during which time, the CO2 monitor is essentially out of service.

If the CO2 monitor is determined to be in either the purge or calibration cycle, the CPU will start a timer, preferably for about thirty seconds, and at the end of that time it will again inquire as to whether the CO2 monitor is still in the purge or calibration cycle. If, at that time the CO2 monitor is still in either of such cycles, the CPU will recognize that something is wrong and will again immediately force the volume monitor 22 active to trigger the apnea alarm 20 in the event of a fault condition. Again, the attempt by the user to disable such alarm is negated.

If, on the other hand, at the end of the timed cycle, the CPU determines that the CO2 monitor has passed though the purge or calibration cycle, it will run a further check to see if the CO2 monitor itself is fully functional. That step is also taken if, in the previous inquiry, the query as to the activity of the purge and calibration cycles had come back negative indicating that the CO2 monitor was not in either of such cycles.

The final step, therefore, is to determine if anything else is not functioning properly with the CO2 monitor. If at this step anything is found indicating that the CO2 monitor is not fully functional, the system again will immediately force the apnea alarm to receive a fault condition signal from the volume monitor to carry out the alarm function. If, on the other hand, the CO2 monitor is found to be fully functional, the present system will accept the users selection to disable the apnea alarm based on input from the volume monitor and that function of the alarm is disabled.

Thus, whereas in the prior art, it was not possible for the user to disable the triggering of the apnea alarm by means of a fault signal from the volume monitor when the anesthesia ventilator was in the mechanical ventilation mode, in accordance with the present invention, the user can now disable such alarm, however the selection to disable the alarm will be refused or later overridden if there is any reason to suspect that the CO2 monitor is not fully functional and capable of properly triggering the apnea alarm on its own.

While the invention has been disclosed and described with respect to a single embodiment, it will become apparent the variations and modifications may be made therein, and it is therefore intended in the following claims to cover each such variation and modification as falls within the true spirit and scope of the invention.

We claim:

1. In an anesthesia system for providing an anesthetizing gas to a patient through a patient circuit, and including an anesthesia ventilator having a mechanical ventilation mode, a $CO_2$ monitor for monitoring the level of $CO_2$ in the patient circuit, a volume monitor for monitoring the volume of exhalation from the patient into the breathing circuit and an apnea alarm responsive to a predetermined fault condition in the $CO_2$ level detected by the $CO_2$ monitor and a predetermined fault condition in the exhaled breath of the patient detected by the volume monitor, the improvement comprising a system to allow the disablement of the apnea alarm from responding to the volume monitor, said system comprising means to determine when the $CO_2$ monitor is capable and incapable of communicating the predetermined fault condition to trigger the apnea alarm, means to selectively disable the apnea alarm from responding to the fault condition detected by the volume monitor when said system has determined $CO_2$ monitor is capable of triggering the apnea alarm, and said system further including means to reactivate said volume monitor to trigger said apnea alarm whenever said system determines said $CO_2$ monitor is no longer capable of triggering said apnea alarm.

2. A system for disabling said apnea alarm based upon said volume monitor as described in claim 1 wherein said system includes a CPU that queries said CO2 monitor to determine the capable or incapable condition of said CO2 monitor.

3. A system for disabling said apnea alarm based upon said volume monitor as described in claim 2 wherein said means to determine when said $CO_2$ monitor is capable or incapable of triggering the apnea alarm operates at predetermined time intervals.

4. A system for disabling said apnea alarm based upon said volume monitor as described in claim 3 wherein said means to determine when said $CO_2$ monitor is capable or incapable of triggering the apnea alarm operates at timed intervals of about thirty seconds.

5. A method of allowing the selective disablement of an apnea alarm in an anesthesia system including a $CO_2$ monitor monitoring the $CO_2$ in a patients circuit and a volume monitor monitoring the volume of breath expired by the patient, an apnea alarm activated by a signal from either of the $CO_2$ and volume monitors upon detection, respectively, of a predetermined fault condition detected in the $CO_2$ level in the patients circuit and in the volume of the patients exhalation comprising the steps of:

(a) activating a signal to disable the input from the volume monitor to trigger the apnea alarm, (b) monitoring the status of the $CO_2$ monitor to determine whether it is capable or incapable of providing its signal to activate the apnea alarm, and (c) preventing the signal activated in step (a) from disabling the input from the volume monitor to the apnea alarm if the $CO_2$ monitor is determined in step (b) to be incapable of providing its signal.

6. A method as defined in claim 5 further including the steps of (d) determining whether the CO2 monitor is disabled due to a temporary disablement, (e) Allowing the passage of a predetermined time period and (f) repeating step (d) above.

7. A method as defined in claim 5 wherein the step (b) is repeated continuously at predetermined intervals.

* * * * *